United States Patent [19]

Sy

[11] Patent Number: 5,113,031

[45] Date of Patent: * May 12, 1992

[54] AROMATIC ALKYLATION PROCESS

[76] Inventor: Angel Sy, 1510 Mission Spring Dr., Katy, Tex. 77450

[ * ] Notice: The portion of the term of this patent subsequent to Feb. 4, 2009 has been disclaimed.

[21] Appl. No.: 611,104

[22] Filed: Nov. 9, 1990

[51] Int. Cl.$^5$ ............................................. C07C 2/68
[52] U.S. Cl. ................................. 585/467; 585/446; 585/447; 203/DIG. 3; 203/DIG. 6
[58] Field of Search ............ 203/DIG. 3, DIG. 6; 585/446, 447, 467

[56] References Cited

U.S. PATENT DOCUMENTS

| | | | |
|---|---|---|---|
| 4,316,997 | 2/1982 | Vaughan | 585/458 |
| 4,371,714 | 2/1983 | Young | 568/791 |
| 4,423,254 | 12/1983 | Olah | 568/793 |
| 4,469,908 | 9/1984 | Burress | 585/467 |
| 4,540,831 | 9/1985 | Briggs | 568/697 |
| 4,849,569 | 7/1989 | Smith, Jr. | 585/446 |
| 4,950,834 | 8/1990 | Arganbright et al. | 585/446 |

Primary Examiner—Patrick P. Garvin
Assistant Examiner—E. D. Irzinski
Attorney, Agent, or Firm—Kenneth H. Johnson

[57] ABSTRACT

A process for the catalytic distillation production of alkylated aromatic compounds is provided wherein the vapor pressure of the olefin may be increased while maintaining the same olefin feed rate and aromatic to olefin ratio. In one embodiment a side stream from the vapor from the second column below the catalyst and olefin feed is condensed and rerouted to the aromatic make up stream from the reflux drum. The vapor pressure of the olefin in the lower end of the first column in the catalyst bed is thus increased which increases the equilibrium concentration of the olefin in the liquid phase. In another embodiment of the invention the effective driving force for the reaction is increased by injecting the olefin at different heights within the catalyst bed. If additional olefin is injected more catalyst bed height would be required, but the additional catalyst is more that offset by the increased throughput at the same overall olefin conversion. The practice of injecting the olefin feed at different heights is especially useful when the same olefin feed rate is used but split among the several streams because less catalyst is required.

2 Claims, 4 Drawing Sheets

AROMATIC ALKYLATION PROCESS

BACKGROUND OF THE INVENTION

1. Field of the Invention

The present invention relates to a catalytic distillation process for the alkylation of organic aromatic compounds with olefins over an acidic catalytic distillation structure. More particularly the invention relates to an improvement in the process whereby the olefin concentration in the liquid phase is increased by increasing the olefin partial pressure in the vapor phase while maintaining a constant olefin feed rate and benzene to olefin ratio.

2. Related Art

Alkylation of organic aromatic compounds using catalytic distillation has been disclosed in U.S. Pat. No. 4,849,569 issued to Lawrence A. Smith, Jr. As practiced the process disclosed therein is embodied by two separate columns connected by liquid and vapor flow lines with one column being filled with a bed of the catalytic distillation structure and the second containing standard distillation structure. The olefin is fed below the catalyst bed, usually into the top of the second column. The aromatic compound is fed with the reflux into the top of the first column above the catalyst bed.

Theoretically the two columns should act as one continuous column. Increasing the olefin concentration in the vapor will increase the equilibrium olefin concentration in the liquid phase and thus the driving force for the reaction; resulting in a more economical process. However, the effect on the projected catalyst life may be deleterious as it has been found that a key variable in catalyst aging is the concentration of the olefin in the liquid phase in contact with the catalyst. Another associated effect is a decrease in the liquid benzene loading throughout the system which detrimentally affects the reaction kinetics and selectivities due to the reduction in the critical benzene to olefin ratio.

SUMMARY OF THE INVENTION

Briefly the invention is an improvement of the process for the alkylation of organic aromatic compounds which utilizes catalytic distillation wherein the improvement comprises the ability to increase the olefin vapor pressure in the catalyst bed while maintaining the olefin feed rate and the olefin to aromatic ratio. In one embodiment a side stream from the vapor from the second column below the catalyst and olefin feed is condensed and rerouted to the aromatic make up stream from the reflux drum. The vapor pressure of the olefin in the lower end of the first column in the catalyst bed is thus increased which increases the equilibrium concentration of the olefin in the liquid phase. In a similar embodiment a refluxed enriching section is added to the second column above the liquid feed from the first column which improves the vapor quality.

In another embodiment of the invention the effective driving force for the reaction is increased by injecting the olefin at different heights within the catalyst bed. If additional olefin is injected more catalyst bed height would be required, but the additional catalyst is more than offset by the increased throughput at the same overall olefin conversion. However, the practice of injecting the olefin feed at different heights is especially useful when the same olefin feed rate is used but split among the several streams because less catalyst, hence a smaller reactor is required for the same alkylation throughput. dr

DESCRIPTION OF THE PREFERRED EMBODIMENTS

For an understanding of the present invention the reader should first be familiar with previous design practices and operation. For a detailed description of the general principles associated with the alkylation of organic aromatic compounds utilizing the catalytic distillation process, the reader is referred to the above mentioned U.S. Pat. No. 4,849,569.

Figure 1:
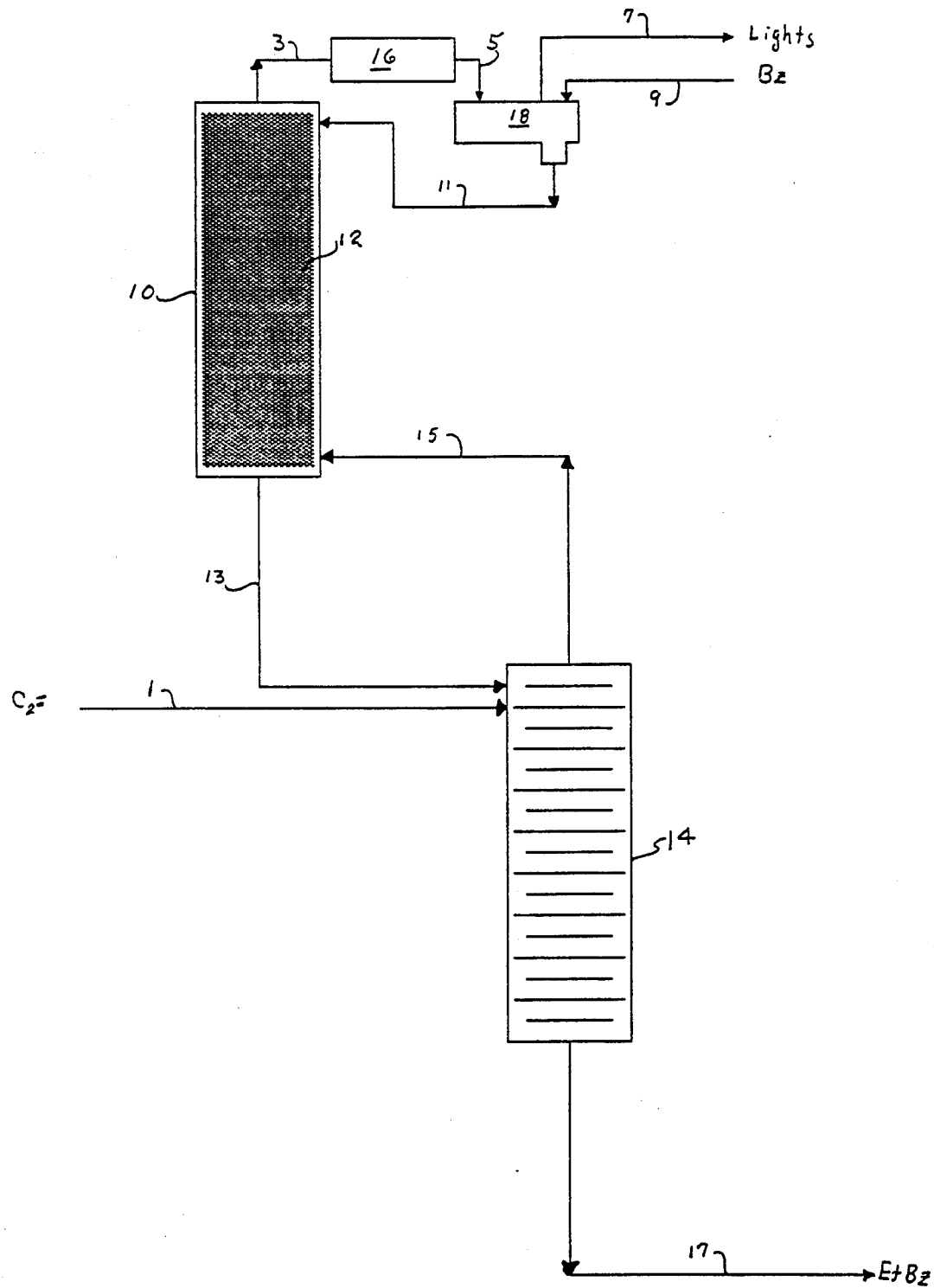
FIG. 1 is a simplified flow diagram in schematic form as the process was formerly practiced.

FIG. 1 shows in a very simplified form the previous design practice for organic aromatic alkylation as embodied in the production of ethylbenzene from the reaction of benzene with ethylene. Other organic aromatic compounds and olefins may be used as feeds yielding different products or product mixes. Additionally, polysubstituted aromatic compounds may also be produced and separated for transalkylation.

The previous operation utilizes a distillation column reactor having an "upper" column lo containing the particulate acid catalyst 12 in the form of catalytic distillation structures. This "upper" column is commonly referred to as the distillation reaction zone. A "lower" column 14 contains standard distillation structure and is referred to as the benzene stripper which completes the separation of unreacted benzene from the higher boiling reaction products—ethylbenzene and polysubstituted aromatic compounds. In this operation the olefin is fed via flow line 1 to the top of the benzene stripper 14 and make up benzene is fed to the reflux drum 18 via flow line 9. Essentially all of the olefin is converted in the distillation reaction zone 12 so that only benzene and any inert lights are taken overhead via flow line 3, condensed in partial condenser 16 and separated in reflux drum 18. The uncondensed light inerts are removed via flow line 7.

The bottoms from the "upper" column 12, containing the higher boiling reaction products and some unreacted benzene are fed via line 13 to the upper end of the benzene stripper 14 where the reaction products, predominantly ethylbenzene, are removed as bottoms via line 17 for further processing if desired.

In the previous design the upper column 10 containing the distillation reaction zone behaves as a packed absorber column. For a fixed volume of catalyst, the olefin absorption rate into the liquid phase is limited by the average partial pressure of olefin in the vapor phase as it travels upward through the distillation reaction zone 12. As the effective volume of catalyst decreases due to aging, higher average olefin partial pressure is required to maintain the minimum olefin conversion.

The process embodied in the present invention provides the capability to raise this driving force and allows variation of the driving force at will during the life of the catalyst.

Figure 2:
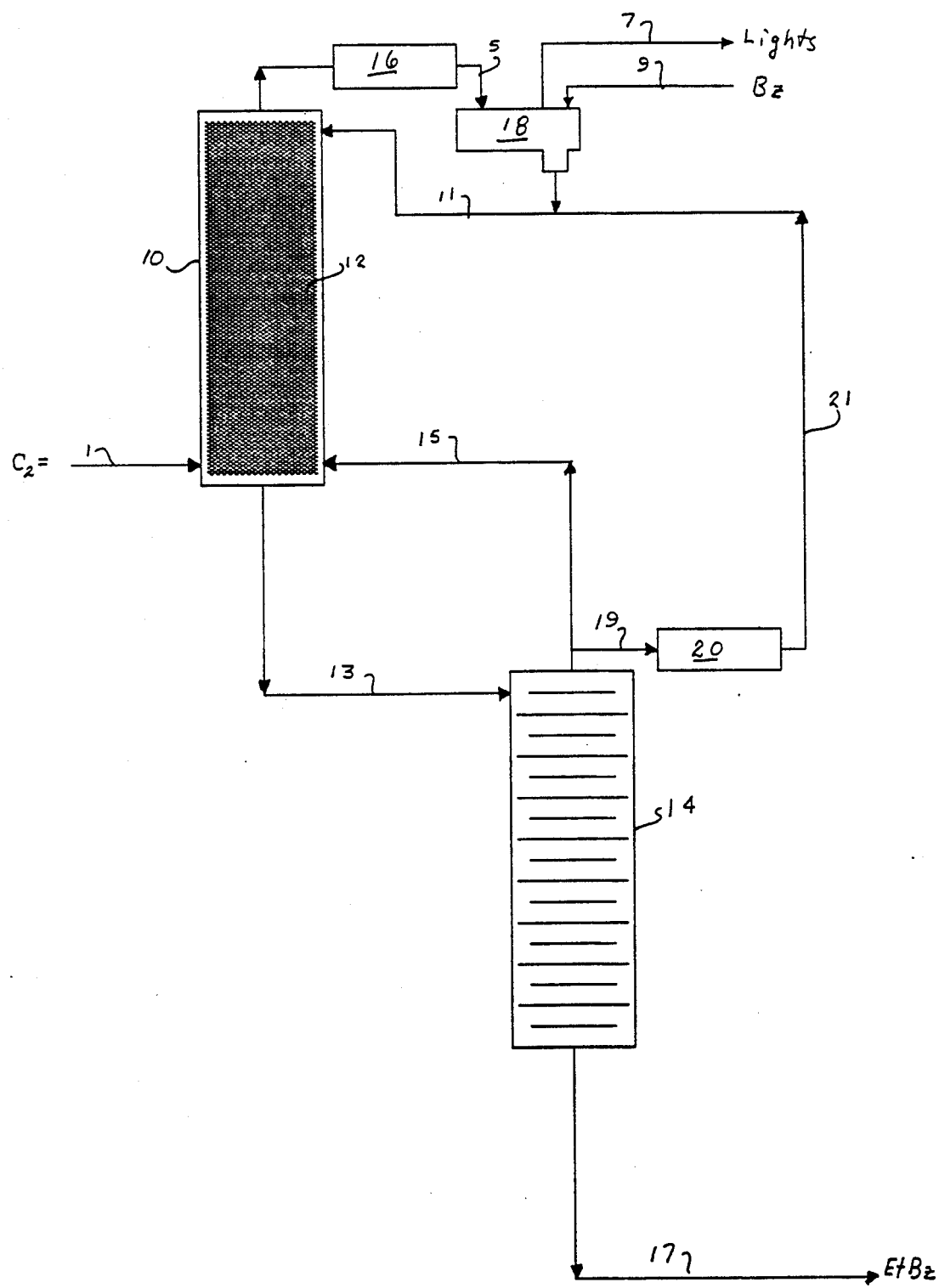
FIG. 2 is a simplified flow diagram in schematic form showing one embodiment of the present invention.

In a first embodiment as shown in FIG. 2 a condenser 20 is provided to condense a slip stream 19 of the vapor from the benzene stripper 14. The olefin feed line 1 is moved to the bottom of the "upper" column 10 to prevent any of the olefin from being withdrawn with the slip stream. The olefin feed line 1 could be injected into the vapor return line 15 upstream of the slip stream draw off. The slip stream 19 lowers the concentration of benzene in the vapor and thus increases the olefin concentration at the lower end of the distillation reaction zone 12. The condensed liquid from the condenser 20 is routed via line 21 to the top of the distillation reaction zone 12 by combining it with the reflux in line 11. Thus the critical benzene to olefin ratio in the distillation reaction zone 12 is maintained. Alternatively, the condenser 20 may be used as a knock back condenser with the condensed liquid being returned to the top of the benzene stripper or used elsewhere in the process and the reduced vapor flowing on to the "upper" column via flow line 15.

Figure 3:
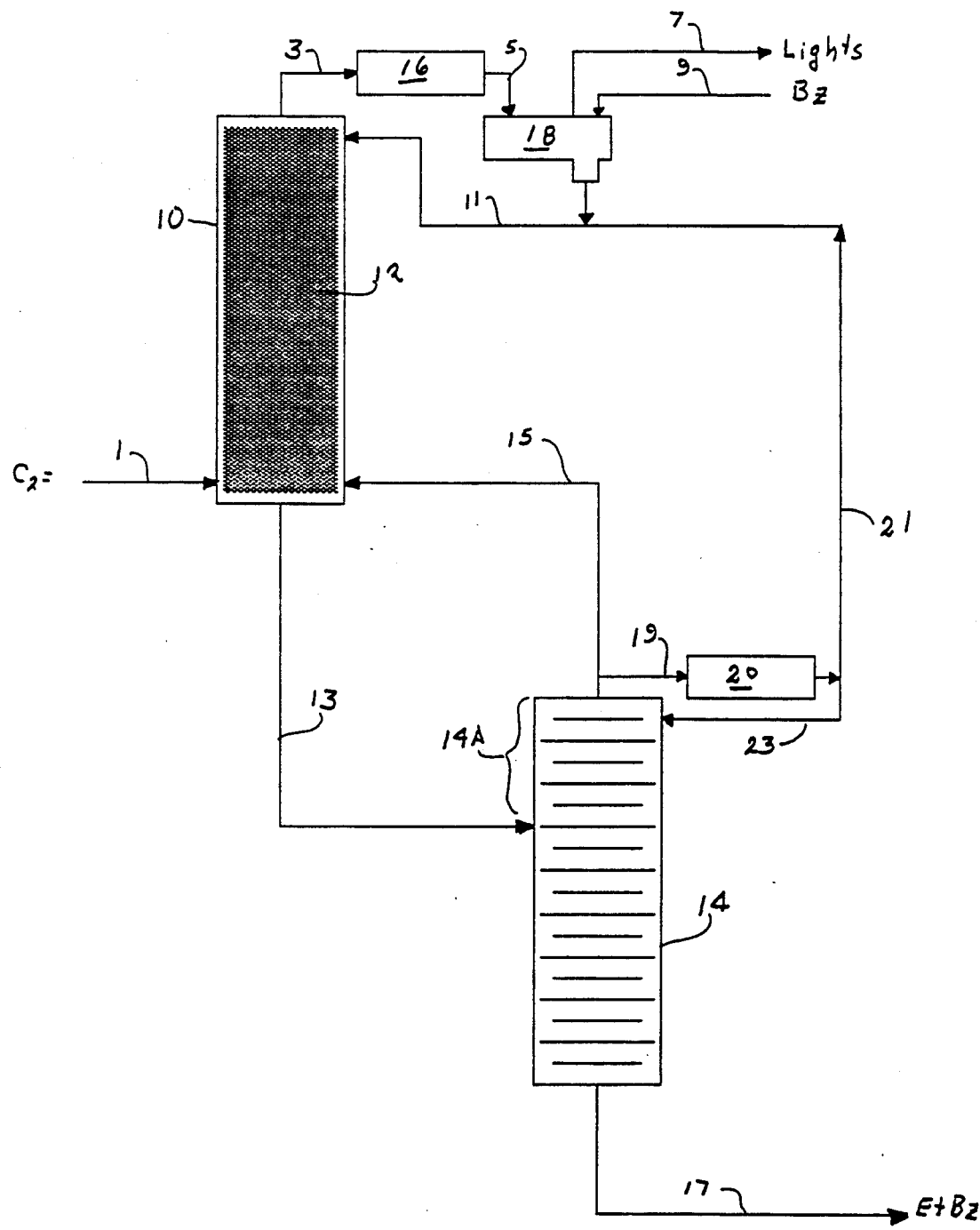
FIG. 3 is a simplified flow diagram in schematic form showing a second embodiment of the present invention.

A second embodiment is shown in FIG. 3. A Short enriching section 14A is added above the liquid inlet to the benzene stripper to provide more efficient separation in the stripper 14. If desired, the enriching section 14A may include a reflux via line 23 as shown. In either case a reduced vapor enriched in benzene is provided to the bottom of the distillation reaction zone.

Figure 4:
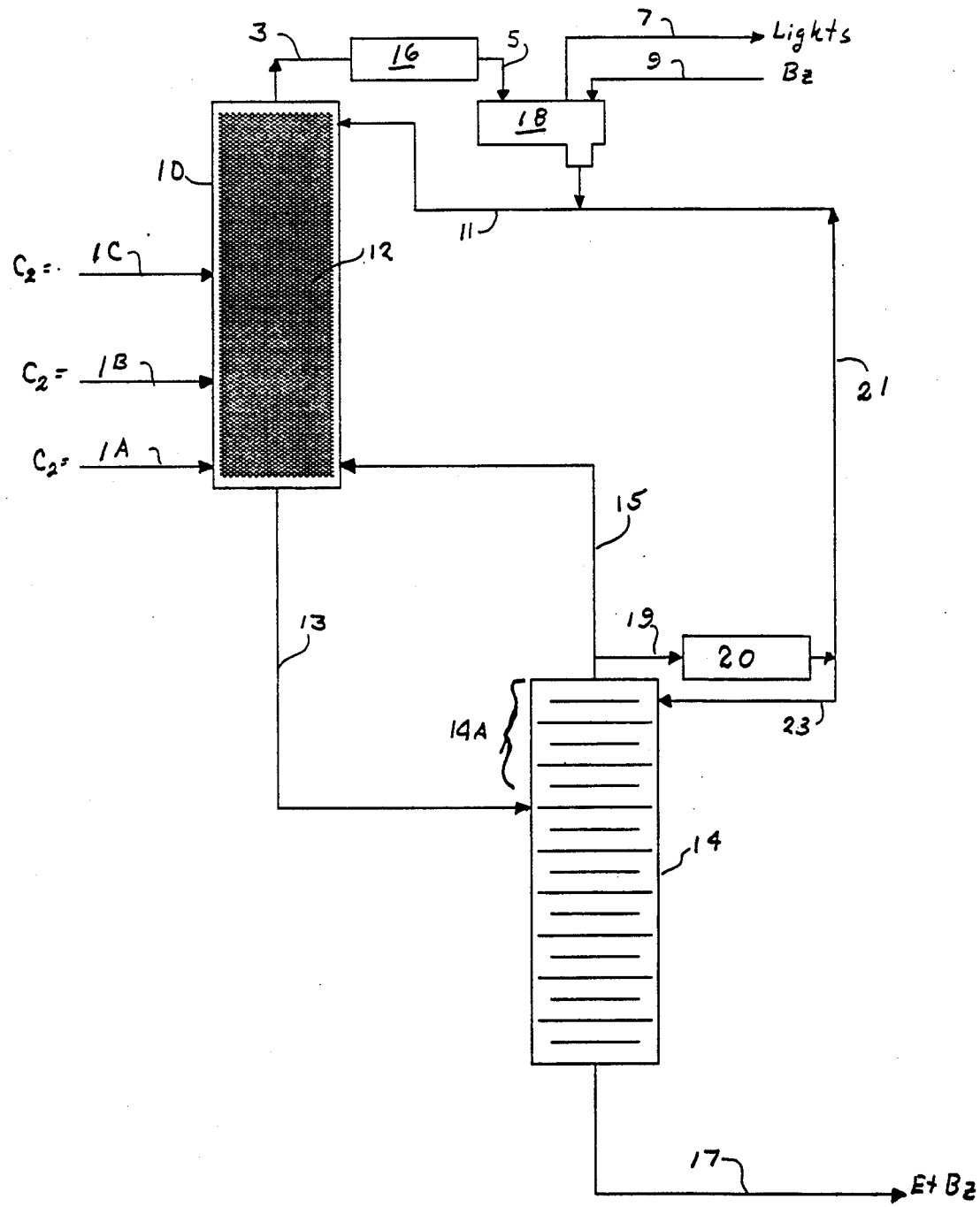
FIG. 4 is a simplified flow diagram in schematic form showing a third embodiment of the present invention.

In a third embodiment shown in FIG. 4 the olefin partial pressure is effectively increased by dividing the olefin feed in to several streams and feeding at different heights in the distillation reaction zone 12. Although there is no actual increase in the olefin this improvement extends the cycle time with a resultant increase in olefin in the liquid phase.

Under the process as described by FIG. 1 the partial pressure of the olefin in the vapor phase is highest at the bottom and lowest at the top due to the progressive reaction up through the reaction zone bed 12. The equilibrium concentration in the liquid phase follows the same profile. In a pilot unit demonstration plant having 29 feet of catalyst height in the distillation reaction zone, the overall conversions of olefin at six feet and twelve feet above the bottom of the bed are about 40 and 63% respectively. These conversions represent a driving force reduction of about 40% per six feet of bed.

If additional olefin is fed instead of simply dividing the same feed stream, it should be appreciated that additional bed height would be necessary to ensure that the overall conversion of the combined olefin feed remains at an acceptable level. However, an unexpected result is that the extra throughput of olefin obtainable at the same overall conversion is beyond that which would be expected by the simple addition of olefin and catalyst height. At a constant olefin feed rate this converts into less catalyst flow area needed for the same height of catalyst and conversion level. For simplicity the following cases are presented for double olefin feed points, but can be applied to any number of feed points limited only by practical considerations.

Case 1

An additional six foot catalyst bed is installed above the top bed of the original five bed reaction distillation zone (30 feet original bed height). Additional olefin equal to about 40% of the original amount fed at the bottom of the zone is fed between the bottommost bed and the next higher. All of the olefins are in contact with at least 30 feet of catalyst and the overall conversion of the combined olefin feed is more than maintained. The advantage that is realized is that a 40% increase in olefin throughput can be achieved with only a 20% increase in additional bed height. At a constant throughput this represents a reduction in the cross sectional area of the distillation reaction zone of about 30% and a net reduction in the required catalyst volume of about 20%.

Case 2

Two additional six foot beds are added to the standard five bed arrangement for a total bed height of 42 feet. Additional olefin of 63% of the original amount is fed between the second and third beds from the bottom. Again all of the olefin contacts at least 30 feet of catalyst to achieve the same overall conversion rate. The advantage thus gained is that a 63% increase in throughput is achieved with only a 40% increase in bed height. At constant throughput this represents a reduction in cross section area of 40% and a 20% reduction in catalyst volume requirement.

The invention claimed is:

1. In a catalytic distillation process for the alkylation of organic aromatic compounds with olefins over a particulate acidic catalytic distillation structure comprising the steps of feeding a stream containing olefins and a stream containing organic aromatic compounds to a distillation column reactor and concurrently reacting the olefins and organic aromatic compounds and separating the resulting reaction product by fractional distillation, the improvement comprising the increasing the olefin partial pressure through out the catalyst bed while maintaining a constant olefin feed rate and maintaining a constant aromatic compound to olefin ratio, wherein the effective olefin partial pressure is increased by dividing the olefin feed into at least two separate streams and feeding said separate streams at different locations along said catalyst bed.

2. A process for the alkylation of organic aromatic compounds with olefins, comprising the steps of:
   (a) dividing a first stream containing olefins into a second and third streams of the same composition and feeding said second and third streams to a distillation column reactor at different heights in a distillation reaction zone and feeding a fourth stream containing organic aromatic compounds to said distillation column reactor near the top of said distillation reaction;
   (b) contacting said olefins and said organic aromatic compounds together with a particulate acidic catalytic distillation structure in said distillation reaction zone thereby reacting substantially all of said olefins with a portion of said organic aromatic compounds to form a reaction mixture containing alkylated aromatic product and unreacted organic aromatic compounds while distilling a portion of said unreacted organic aromatic compounds overhead of said distillation column reactor and distilling said alkylated aromatic product and the remainder of said unreacted organic aromatic compounds downward out of said distillation reaction zone; and
   (c) separating said alkylated product from said remainder of unreacted organic aromatic compounds by fractional distillation in a separate distillation zone, said remainder of unreacted organic aromatic compounds being recovered as overheads from said distillation zone and said alkylated product being recovered as bottoms from said distillation zone.

* * * * *